United States Patent [19]

Defossa et al.

[11] Patent Number: 5,556,850

[45] Date of Patent: * Sep. 17, 1996

[54] CRYSTALLINE ACID ADDITION SALTS OF DIASTEREOMERICALLY PURE 1-(2,2-DIMETHYL-PROPIONYLOXY)-ETHYL-3-CEPHEM-4-CARBOXYLATE

[75] Inventors: Elisabeth Defossa, Idstein; Gerd Fischer, Limburg; Joachim-Heiner Jendralla, Frankfurt am Main; Rudolf Lattrell, Königstein/Taunus; Theodor Wollmann, Hofheim am Taunus; Dieter Isert, Eschborn, all of Germany

[73] Assignee: Hoechst Aktiengesellschaft, Frankfurt am Main, Germany

[*] Notice: The term of this patent shall not extend beyond the expiration date of Pat. No. 5,100,887.

[21] Appl. No.: 447,635

[22] Filed: May 23, 1995

Related U.S. Application Data

[63] Continuation of Ser. No. 886,143, May 21, 1992, abandoned.

[30] Foreign Application Priority Data

May 21, 1991 [DE] Germany ............... 41 16 937.9

[51] Int. Cl.$^6$ ................ C07D 501/32; A61K 31/545
[52] U.S. Cl. .............................. 514/202; 540/222
[58] Field of Search ................ 540/222; 514/202

[56] References Cited

U.S. PATENT DOCUMENTS

| | | |
|---|---|---|
| Re. 34,865 | 3/1992 | Adam et al. . |
| 4,098,888 | 7/1978 | Ochiai et al. . |
| 4,203,899 | 5/1980 | Ochiai et al. . |
| 4,205,180 | 5/1980 | Ochiai et al. . |
| 4,264,595 | 4/1981 | Numata et al. . |
| 4,278,793 | 7/1981 | Dürckheimer et al. . |
| 4,283,396 | 8/1981 | Heymes et al. . |
| 4,298,606 | 11/1981 | Ochiai et al. . |
| 4,355,160 | 10/1982 | Ochiai et al. . |
| 4,409,215 | 10/1983 | Takaya et al. . |
| 4,462,999 | 7/1984 | Takaya et al. . |
| 4,483,855 | 11/1984 | Nakao et al. . |
| 4,486,425 | 12/1984 | Nakao et al. . |
| 4,514,565 | 4/1985 | Ochiai et al. . |
| 4,668,783 | 5/1987 | Ochiai et al. . |
| 4,904,652 | 2/1990 | Takaya et al. . |
| 4,912,212 | 3/1990 | Ochiai et al. . |
| 4,973,684 | 11/1990 | Ochiai et al. . |
| 4,992,431 | 2/1991 | Heymes et al. . |
| 5,026,695 | 6/1991 | Takaya et al. . |
| 5,100,887 | 3/1992 | Adam et al. .............. 540/228 |
| 5,409,918 | 4/1995 | Adam et al. . |

FOREIGN PATENT DOCUMENTS

| | | |
|---|---|---|
| 0029557A2 | 6/1981 | European Pat. Off. . |
| 0034536B1 | 8/1981 | European Pat. Off. . |
| 0034536A2 | 8/1981 | European Pat. Off. . |
| 0049119A2 | 4/1982 | European Pat. Off. . |
| 0134420A2 | 3/1985 | European Pat. Off. . |
| 0329008A2 | 8/1989 | European Pat. Off. . |
| 0402806A1 | 6/1990 | European Pat. Off. . |
| 2556736A2 | 6/1976 | Germany . |
| 2560398C2 | 9/1983 | Germany . |
| 3804841A1 | 8/1989 | Germany . |
| 3919259A1 | 12/1990 | Germany . |

OTHER PUBLICATIONS

T. Nishimura et al., Orally Active 1–(Cyclohexyloxycarbonyloxy)alkyl Ester Prodrugs of Cefotiam, XL J. Antibiotics 81–90 (1987).

K. Fujimoto et al., Studies on Orally Active Cephalosporin Esters, XL J. Antibiotics 370–384 (1987).

H. Kamachi et al., Synthesis and Biological Acitivity of a New Cephalosporin, BMY–28232 and its Prodrug–type Esters for Oral Use, XLI J. Antibiotics 1602–16 (1988).

E. Defossa et al., Cefdaloxime Pentexil Tosilate (HR 916 K): A Diastereomerically Pure Novel Oral Cephalosporinester: Synthesis and Antibacterial Actrivity In Vivo, Abstract No. 187, XXXII Interscience Conference on Antimicrobial Agents and Chemotherapy (Anaheim, CA, Oct. 11–14, 1991).

D. Isert et al., Cefdaloxine Pentexil Tosilate (HR 916 K): A Diastereomerically Pure Novel Oral Cephalosporinester With Outstanding Absorption Characteristics, Abstract No. 188, XXXII Interscience Conference on Antimicrobial Agents and Chemotherapy (Anaheim, CA, Oct. 11–14, 1991).

Primary Examiner—Nicholas Rizzo
Attorney, Agent, or Firm—Finnegan, Henderson, Farabow, Garrett & Dunner, L.L.P.

[57] ABSTRACT

The invention relates to crystalline acid addition salt of the two diastereomers of the 1-(2,2-dimethylpropionyloxy)ethyl 3-cephem-4-carboxylate of the general formula II

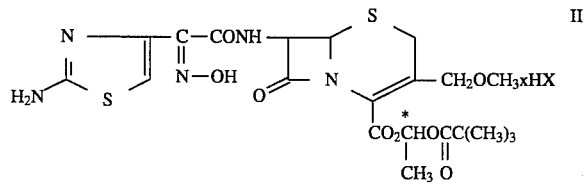

in which X is the anion of a physiologically acceptable, mono- or polybasic, inorganic or organic acid and the group =N—OH is in the syn-position, pharmaceutical formulations which are active against bacterial infections and contain such cephem derivatives, processes for the preparation of the cephem derivatives and the use of the cephem derivatives for combating bacterial infections.

4 Claims, No Drawings

CRYSTALLINE ACID ADDITION SALTS OF DIASTEREOMERICALLY PURE 1-(2,2-DIMETHYL-PROPIONYLOXY)-ETHYL-3-CEPHEM-4-CARBOXYLATE

This application is a continuation, of application Ser. No. 07/886,143, filed May 21, 1992, now abandoned.

The invention relates to crystalline, enterally absorbable salts of the diastereomers of 1-(2,2-dimethylpropionyloxy)-ethyl 7-[2-(2-aminothiazol-4-yl)-2-(Z)-hydroxyimino-acetamido]- 3-methoxymethyl-3-cephem-4-carboxylate of the formula I

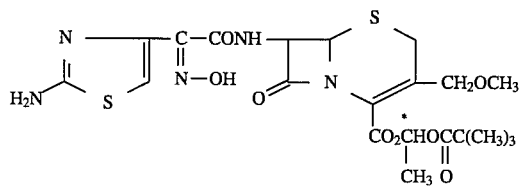

and to processes for their preparation.

Esters of 7-[2-(2-aminothiazol-4-yl)-2-(Z)-hydroxyiminoacetamido]-3-methoxymethyl-3-cephem-4-carboxylic acid have been described in German Patent Application P 38 04 841 (EP-A-0 329 008). Of these, the ester of the formula I is of particular interest, since it is absorbed well enterally in various animal species and after absorption is split again rapidly and completely by endogenous enzymes into antibiotically active cephalosporin containing the free carboxyl group.

Stoichiometric crystalline salts of the ester of the formula I and sulfonic acids were then described in German Patent Application P 39 19 259 (EP-A-0 402 806), these having advantages over the free base of the formula because of their high stability.

The ester of the formula I has an asymmetric carbon atom in the 1-position of the ethyl ester group. The salts described in German Patent Application P 39 19 259 are in the form of mixtures of the diastereomers.

Comparable mixtures of diastereomers are present in cefotiam-hexetil, cefuroxim-axetil, cefpodoxim-proxetil and BMY 28271.

From the studies so far on the mechanism of enteral absorption of such cephem prodrug esters, the stereo-chemistry in the 1-position of the ethyl ester group has no influence on enteral absorbability. This could be demonstrated experimentally for diastereomers of cefotiam-hexetil (T. Nishimura et al., The Journal of Antibiotics, Volume XL (1987) 81–90).

It was therefore very surprising that salts of the separated diastereomers of the formula I show distinct differences in enteral absorption, so that the diastereomer which is absorbed better showed a higher bioavailability than the mixture of diastereomers described in German Patent Application P 39 19 259.

The present invention therefore relates to diastereomerically pure salts of the general formula II in which the group =N—OH is in the syn-position. The preferred diastereomer is the less polar of the two diastereomers with the (1S)-configuration in the ester part, which has the higher bioavailability.

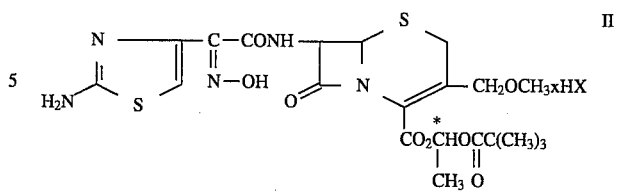

In the general formula II, HX is a mono- or polybasic acid, in which X can be an inorganic or organic, physiologically acceptable anion.

An inorganic acid HX is, for example, a stoichiometric amount of HCl, HBr, HI, HBF$_4$, HNO$_3$, HClO$_4$, H$_2$SO$_4$ or H$_3$PO$_4$. HX as an organic acid is an aliphatic or aromatic sulfonic acid. The inorganic acids HCl, HBr and H$_2$SO$_4$ and the organic acids methanesulfonic acid, ethanesulfonic acid, benzenesulfonic acid, p-toluenesulfonic acid and 4-ethylbenzenesulfonic acid are preferred. Benzenesulfonic acid, p-toluenesulfonic acid and 4-ethylbenzenesulfonic acid are especially preferred.

The invention furthermore relates to processes for the preparation of diastereomeric compounds of the general formula II, which comprise 1. preparing a compound of the formula III

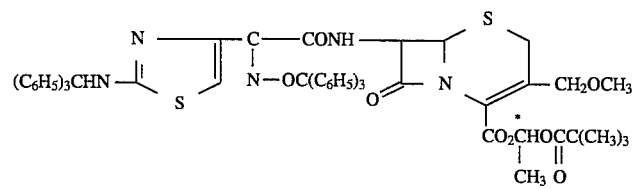

separating the diastereomers by chromatography, splitting off the trityl groups and preparing the acid addition products, or
2. concentrating the less polar diastereomer from the mixture of diastereomers of the formula II by crystallization, or
3. preparing an intermediate stage of the formula IV in the form of the separated diastereomers

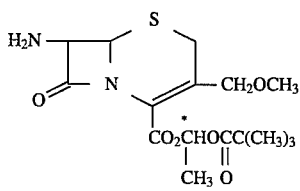

and converting this stage into the separated diastereomers of the formula II.

The preparation of the diastereomer mixture of the formula III required in Process 1 has already been described in German Patent Application P 38 04 841.

The diastereomers are separated by chromatography on silica gel using a mobile phase of toluene and ethyl acetate. The ratio of toluene to ethyl acetate can be varied widely and is between 3:1 and 20:1, the range from 10:1 to 15:1 being preferred. 20–80 parts of silica gel are employed for the separation per part of mixture to be separated, 30–50 parts being preferred.

The pure diastereomers of the formula III thus obtained are converted into the salts of the formula II by methods which have already been described for the diastereomer mixture in German Patent Applications P 38 04 841 and P 39 19 259.

In Process 2, the less polar diastereomer of the formula II is also obtained by crystallization of the diastereomer mixture from organic solvents.

Under the customary conditions of recrystallization, a substance is dissolved in a solvent by heating to the boiling point. Compounds of the formulae I and II decompose under these conditions. The route described below nevertheless allows recrystallization of the salts.

One part of the diastereomer mixture is first dissolved in 1–5 parts, preferably 1–2 parts, of an organic solvent, such as, for example, dimethylformamide or dimethylacetamide. The solution thus obtained is added dropwise to 5 to 50 times the volume of an organic solvent (for example alcohol, ester, ether, ketone or nitrile), such as, for example, methanol, ethanol, n-propanol, iso-propanol, n-butanol, iso-butanol, tert-butanol, ethyl acetate, butyl acetate, acetone, diethyl ether, diisopropyl ether or acetonitrile. 10–20 times the volume of n-propanol, iso-propanol or n-butanol is particularly preferred here.

The duration of the dropwise addition can be between 10 minutes and 2 hours, preferably between 30 minutes and 1 hour. The mixture is subsequently stirred for a further 1–18 hours, preferably 3–6 hours, to bring the crystallization to completion. The temperature should preferably be between 0° C. and 40° C., 20°–25° C. being preferred.

The salts thus obtained are isolated by customary laboratory processes, such as, for example, filtration, and freed from adhering solvents under a high vacuum (<1 torr) in the presence of a drying agent, such as, for example, phosphorus pentoxide.

The diastereomer having a higher enteral absorption of the formula II (HX: p-toluenesulfonic acid) is obtained in a pure form by repeating the operation described above several times.

In Process 3, the compound of the formula IV is prepared, as has been described in German Patent Application P 38 04 841, as a mixture of the diastereomers.

The diastereomers can be separated by crystallization of salts of the formula V

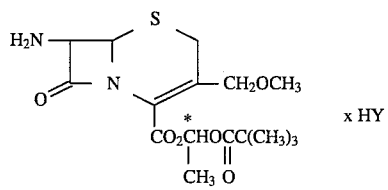

x HY    V

In the general formula V, HY is a mono- or polybasic acid, in which Y can be an inorganic or organic anion.

HY as an inorganic acid is, for example, HCl, HBr, HI, HF, $HNO_3$, $HClO_4$, HSCN, $H_2SO_4$ or $H_3PO_4$. HY as an organic acid is an aliphatic or aromatic sulfonic acid, carboxylic acid or phosphonic acid. The following organic acids, for example, can thus be employed: benzenesulfonic acid, p-toluenesulfonic acid, 4-ethylbenzenesulfonic acid, 4-chlorobenzenesulfonic acid, 4-bromobenzenesulfonic acid, 2-mesitylenesulfonic acid, 4-biphenylsulfonic acid, naphthalene-1,5-disulfonic acid, methanesulfonic acid, ethanesulfonic acid, dodecylsulfonic acid, camphorsulfonic acid and oxalic acid.

Acid components which must be regarded as preferred are: HCl, HBr, benzenesulfonic acid, p-toluenesulfonic acid, 4-ethylbenzenesulfonic acid and 4-biphenylsulfonic acid.

The salt of the formula V is prepared by bringing together a solution of the diastereomer mixture of the formula IV and a solution of the acid component HY. Organic solvents which can be employed are, for example, esters, ethers, alcohols, ketones, hydrocarbons, nitriles and halogenated hydrocarbons, and mixtures thereof. Preferred solvents are, for example, benzene, toluene, ethyl acetate, butyl acetate, methanol, ethanol, n-propanol, iso-propanol, tert-butanol, diisopropyl ether, acetonitrile, methylene chloride, acetone and mixtures thereof.

Water can also be employed as a solvent for inorganic acids if the organic solvent is miscible with water. Solutions of HCl and HBr in organic solvents can be produced, for example, by units of hydrogen chloride or hydrogen bromide or also from acetyl halides, phosphorus halides and phosphorus oxyhalides and an alcohol (halogen=Cl or Br).

The ratio of the base of the formula IV to the acid component is important for concentration of a diastereomer. 0.2–2.0, preferably 0.3 to 1.0 equivalents of acid component should be employed for one equivalent of the diastereomer mixture.

The acid component is added at room temperature. The mixture is subsequently stirred for up to a further 10 hours, depending on the acid component and the solvent, to bring the precipitation to completion. If appropriate, the mixture must be cooled to temperatures between room temperature and −78° C. to bring the precipitation to completion.

If necessary, the salts obtained after filtration are further purified by crystallization. The solvents described above and mixtures thereof are employed for this purpose. The choice of the optimum solvent depends on the acid component used. Thus, for example, methanol, ethanol, n-propanol and iso-propanol are suitable for the p-toluenesulfonic acid salt.

The process is characterized in that the precipitation of the diastereomers of the general formula IV takes place in two successive component steps. Thus, for example, the more sparingly soluble diastereomer of the general formula V is precipitated first by bringing together a solution of the diastereomer mixture of the formula IV with a solution of the acid component HY and is separated off by filtration, and the more readily soluble diastereomer of the general formula V is then precipitated from the filtration solution. The acid component HY can be the same or different in the successive component steps, different acid components HY being added in any desired sequence. Thus, for example, by a suitable choice of the acid component HY, the more polar diastereomer of the general formula IV or the more non-polar diastereomer of the general formula IV can first be precipitated as the more sparingly soluble salt.

The two diastereomers of the formula V can be obtained in a pure form by the choice of acid component. Thus, for example, if hydrogen chloride or hydrogen bromide is used, the more polar diastereomer is obtained, while the use of benzenesulfonic acid, 4-ethylbenzenesulfonic acid, biphenylsulfonic acid or p-toluenesulfonic acid gives the less polar diastereomer.

Alternatively, diastereomer mixtures of the formula IV can also be obtained starting from compounds of the formula VI

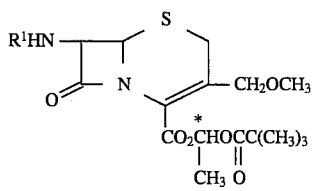

In this formula, the group $R^1$ is an amino-protective group customary in peptide chemistry, such as, for example, the formyl group, the tert-butoxycarbonyl group, the phenoxyacetyl group, the phenylacetyl group, the allyloxycarbonyl group, the benzyloxycarbonyl group and the 4-nitrobenzyloxycarbonyl group.

The protective groups are split off by methods which are known per se. The formyl group and the tert-butoxycarbonyl group can thus be split off, for example, with acid. The phenoxyacetyl group and the phenylacetyl group can be split off, for example, with phosphorus pentachloride or also enzymatically with penicillin acylases. In the case of the allyloxycarbonyl group, the group can be split off with $Pd[P(C_6H_5)_3]_4$. The benzyloxycarbonyl group and the 4-nitrobenzyloxycarbonyl group can be removed hydrogenolytically.

If the phenoxyacetyl group or the phenylacetyl group is split off with phosphorus pentachloride, rapid working up gives the more polar diastereomer in concentrated form as the hydrochloride even without addition of hydrogen chloride. The phosphoric acid ester-chlorides which have not been removed during working up and slowly release hydrogen chloride serve as the source of hydrogen chloride.

Starting from compounds of the formula VI, it is also possible to obtain diastereomerically pure compounds of the formula V by first separating the diastereomers and then splitting off the protective group. The diastereomers can be separated by crystallization or chromatography, the precise conditions depending on the protective group $R^1$. For example, if $R^1$ is the phenoxyacetyl group, the diastereomers can be separated by chromatography on silica gel using an organic solvent mixture.

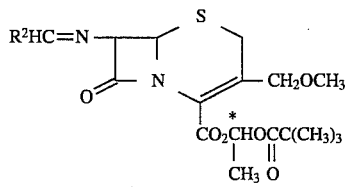

Another alternative for the preparation of pure diastereomers of the formula IV starts from Schiff's bases of the formula VII, in which $R^2$ is a phenyl or naphthyl radical, which can be substituted by ($C_1$–$C_4$)-alkyl, phenyl, methoxy, halogen (for example F, Br, Cl or I) or nitro.

The diastereomer mixture of the Schiff's bases of the formula VII is separated either by chromatography, for example on silica gel, or by fractional crystallization. The Schiff's bases are split back into the pure diastereomers of the formula IV by methods which are known per se, for example by acid hydrolysis or by means of Girard T reagent.

The diastereomeric bases of the formula IV are prepared from the diastereomerically pure salts of the formula V by known methods, and these products are converted into the diastereomeric salts of the formula II as described in German Patent Applications P 38 04 841 and P 39 19 259.

The usefulness of the present invention lies in an increased enteral absorption of the less polar diastereomer of the formula II, as is shown in Table 1 for the p-toluenesulfonic acid salt.

TABLE 1

| Diastereomer composition | Recovery rate (Mean of four experiments) |
|---|---|
| Diastereomer 1 from Example 1 | 67.7% |
| Diastereomer 2 from Example 1 | 19.7% |
| Diastereomer mixture (ratio 1/1) | 39.2% |

Table 1 shows the recovery rate (0–24 hours) of 7-[2-(2-aminothiazol-4-yl)-2-(Z)-hydroxyiminoacetamido]-3-methoxymethyl-3-cephem-4-carboxylic acid in the urine of dogs (n=4) after oral administration of the p-toluenesulfonate of 1-(2,2-dimethylpropionyloxy)ethyl 7-[2-(2-aminothiazol-4-yl)-2-(Z)-hydroxyiminoacetamido]-3-methoxymethyl-3-cephem-4-carboxylate (dose: 10 mg/kg, based on the antibacterially active compound). The amount of active compound in the urine was determined microbiologically by an agar diffusion test using Mueller-Hinton agar (with 10% sheep's blood) and Streptococcus pyogenes A77 as the test germ.

The compounds of the general formula II according to the invention are administered orally in the form of customary pharmaceutical formulations, such as, for example, capsules, tablets, powders, syrups or suspensions. The dose depends on the age, the symptoms and the body weight of the patient and on the duration of the treatment. However, it is as a rule between about 0.1 g and about 5 g daily, preferably between about 0.2 g and about 3 g daily. The compounds are preferably administered in divided doses, for example 2 to 4 times daily, it being possible for the individual dose to contain, for example, between 50 and 500 mg of active compound.

The oral formulations can contain the customary excipients and/or diluents. Thus, for example, binders, such as, for example, gelatin, sorbitol, polyvinylpyrrolidone or carboxymethylcellulose, diluents, such as, for example, lactose, sugar, starch, calcium phosphates or polyethylene glycol, lubricants, such as, for example, talc or magnesium stearate, are possible for capsules or tablets. Syrups or similar known formulation forms are suitable for liquid formulations, for example aqueous or oily suspensions.

The following embodiment examples for diastereomerically pure salts, which can be prepared according to the invention, of the compounds of the formula I, 1-(2,2-dimethylpropionyloxy)ethyl 7-[2-(2-aminothiazol-4-yl)-2-(Z)-hydroxyiminoacetamido]-3-methoxymethyl-3-cephem-4-carboxylate, serve to further illustrate the invention, but do not limit it thereto.

EMBODIMENT EXAMPLE 1

Precursor:
2-(2-Tritylaminothiazol-4-yl)-2-(Z)-trityloxyiminoacetyl chloride 11.4 g (55 mmol) of phosphorus pentachloride, dissolved in 200 ml of anhydrous methylene chloride, are added dropwise to a solution of 42.0 g (54 mmol) of triethylammonium 2-(2-tritylaminothiazol-4-yl)-2-(Z)-trityloxyiminoacetate in 400 ml of anhydrous methylene chloride at −70° C. in the course of 30 minutes such that the internal temperature does not rise above −50° C. After a further 60 minutes at −70° C., the solvent is removed in vacuo, during which the bath temperature should not rise above 30° C. The mixture is then additionally dried briefly under a high vacuum. The crude product thus obtained is dissolved in 100 ml of anhydrous methylene chloride and employed directly for the acylation.

Stage 1:
1-(2,2-Dimethylpropionyloxy)ethyl 3-methoxymethyl-7-[2-(2-tritylaminothiazol-4-yl)-2-(Z)-trityloxyiminoacetamido]-3-cephem-4-carboxylate 9.5 ml (64 mmol) of DBU are slowly added to a suspension of 14.0 g (57 mmol) of 7-amino-3-methoxymethyl-3-cephem-4-carboxylic acid in 160 ml of anhydrous methylene chloride at 0° C. and the mixture is subsequently stirred at 0° C. for 30 minutes. 20.8 g (81 mmol) of 1-iodoethyl 2,2-dimethylpropionate are then added and the mixture is stirred at 0° C. for a further 30 minutes and then allowed to warm to room temperature in the course of 30 minutes. After renewed cooling to 0° C., the crude 2-(2-tritylaminothiazol-4-yl)-2-(Z)-trityloxyiminoacetyl chloride ($\approx$ 54 mmol), dissolved in 100 ml of methylene chloride, is added dropwise and the mixture is then stirred at 0° C. for a further 2 hours. The reaction mixture is concentrated in vacuo and the residue is taken up in ethyl acetate. The mixture is washed successively with 5% sodium thiosulfate solution, saturated sodium bicarbonate solution and saturated sodium chloride solution, and the organic phase is dried over sodium sulfate and concentrated to dryness in vacuo. The crude product is purified by chromatography on silica gel (35–70 μm) (column: 50 cm×8.5 cm, toluene/ethyl acetate=5/1).

Yield: 36.5 g (66%)
The diastereomers are present in a ratio of 1/1.

Stage 2:
Chromatographic separation of the diastereomers 17 g of the diastereomer mixture are chromatographed on silica gel (35–70 μm, column: 46×7.5 cm) using toluene/ethyl acetate (15/1) at a flow rate of 50 ml/minute. After concentration in vacuo, 6.0 g of the non-polar diastereomer 1 and 4.5 g of the polar diastereomer 2 are obtained.

Diastereomer 1:
$R_f$ (toluene/ethyl acetate=5/1): 0.48
$^1$H-NMR (DMSO-$d_6$, 270 MHz): δ=1.15 (s, 9H, C(CH$_3$)$_3$); 1.50 (d, 3H, OCH(CH$_3$)O); 3.20 (s, 3H, OCH$_3$); 3.57 (AB system, 2H, SCH$_2$); 4.15 (s, 2H, CH$_2$O); 5.25 (d, 1H, H-6); 5.89 (dd, 1H, H-7); 6.59 (s, 1H, thiazole H); 6.89 (9, 1H, OCH(CH$_3$)O); 7.12–7.37 (m, 30H, aromatic H); 8.75 (s, 1H, NH); 9.90 (d, 1H, amide NH).

Diastereomer 2:
$R_f$ (toluene/ethyl acetate=5/1): 0.40
$^1$H-NMR (CDCl$_3$, 270 MHz): δ=1.22 (s, 9H, C(CH$_3$)$_3$); 1.56 (d, 3H, OCH(CH$_3$)O); 3.30 (s, 3H, OCH$_3$); 3.39 (AB system, 2H, SCH$_2$); 4.27 (s, 2H, CH$_2$O); 5.05 (d, 1H, H-6); 6.04 (dd, 1H, H-7); 6.41 (s, 1H, thiazole H); 6.75 (s, 1H, NH); 7.04 (q, 1H, OCH(CH$_3$)O); 7.10–7.44 (m, 30H, aromatic H).

Stage 3:
1-(2,2-Dimethylpropionyloxy)ethyl 7-[2-(2-aminothiazol-4-yl)-2-(Z)-hydroxyiminoacetamido]-3-methoxymethyl-3-cephem- 4-carboxylate Diastereomer 1:
3 ml of water are added dropwise to a solution of 6.0 g (5.9 mmol) of diastereomer 1 from Stage 2 in 15 ml of formic acid. The mixture is stirred first at room temperature for 90 minutes and then at 0° C. for 30 minutes. The triphenylcarbinol which has precipitated out is filtered off with suction and rinsed with a little formic acid/water (5/1). 60 ml of ethyl acetate and 20 ml of water are added to the combined filtrates. The pH is brought to 3.0 using 2N sodium hydroxide solution, while cooling in an ice-bath. The organic phase is separated off and washed twice with 50 ml of water each time, and a further 50 ml of water are added. The pH is brought to 6.5 by addition of 40% strength sodium hydroxide solution, during which the internal temperature should not rise above 10° C. After the organic phase has been separated off, it is washed with saturated sodium chloride solution, dried over sodium sulfate and concentrated in vacuo to one quarter of the starting volume. The solution thus obtained is added dropwise to 150 ml of diisopropyl ether. After the mixture has been stirred at room temperature for a further 60 minutes, the product is filtered off with suction, rinsed with diisopropyl ether and dried first in air for 18 hours and then over phosphorus pentoxide in vacuo.

Yield: 1.7 g (54%)
$^1$H-NMR (DMSO-d6, 270 MHz): δ=1.15 (s, 9H, C(CH$_3$)$_3$); 1.48 (d, 3H, OCH(CH$_3$)O); 3.20 (s, 3H, OCH$_3$); 3.55 (AB system, 2H, SCH$_2$); 4.13 (s, 2H, CH$_2$O); 5.21 (d, 1H, H-6); 5.85 (dd, 1H, H-7); 6.65 (s, 1H, thiazole H); 6.87 (q, 1H, OCH(CH$_3$)O); 7.11 (s, 2H, NH$_2$); 9.47 (d, 1H, amide NH); 11.28 (s, 1H, NOH).

Diastereomer 2:
4.5 g (44 mmol) of the diastereomer 2 obtained in Stage 2 are reacted similarly.

Yield: 1.7 g (71%)
$^1$H-NMR (DMSO-d6, 270 MHz): δ=1.16 (s, 9H, C(CH$_3$)$_3$); 1.49 (d, 3H, OCH(CH$_3$)O); 3.20 (s, 3H, OCH$_3$); 3.55 (AB system, 2H, SCH$_2$); 4.12 (s, 2H, CH$_2$O); 5.19 (d, 1H, H-6); 5.82 (dd, 1H, H-7); 6.66 (s, 1H, thiazole H); 6.93 (q, 1H, OCH(CH$_3$)O); 7.10 (s, 2H, NH$_2$); 9.45 (d, 1H, amide NH); 11.29 (s, 1H, NOH).

Stage 4:
p-Toluenesulfonate of 1-(2,2-dimethylpropionyloxy)ethyl 7-[2-(2-aminothiazol-4-yl) -2-(Z)-hydroxyiminoacetamido]- 3-methoxymethyl-3-cephem-4-carboxylate Diastereomer 1:
383 mg (2.0 mmol) of p-toluenesulfonic acid monohydrate in 1 ml of n-propanol are added to a suspension of 1 g (1.85 mmol) of diastereomer 1 from Stage 3 in 35 ml of n-propanol. The solid dissolves, and the salt starts to crystallize after a few minutes. The mixture is stirred at room temperature for a further hour and the product is then filtered off with suction and washed with 5 ml of n-propanol and 10 ml of diisopropyl ether. It is dried first in air for 18 hours and then over calcium chloride and paraffin under a high vacuum.

Yield: 1.09 g (83%) $[\alpha]_D^{20}$=+48 8 (c=1, methanol) Melting point >200° C. (decomposition)
$^1$H-NMR (DMSO-d6, 270 MHz): δ=1.15 (s, 9H, C(CH$_3$)$_3$); 1.48 (d, 3H, OCH(CH$_3$)O; 2.29 (s, 3H, aryl CH$_3$); 3.20 (s, 3H, OCH$_3$); 3.59 (AB system, 2H, SCH$_2$); 4.14 (s, 2H, CH$_2$O); 5.24 (d, 1H, H-6); 5.85 (dd, 1H, H-7); 6.82 (s, 1H, thiazole H); 6.87 (q, 1H, OCH(CH$_3$)O); 7.08–7.15 and 7.45–7.52 (2×m, 2×2H, aromatic H); 8.0–8.8 (broad, 3H, NH$_3$); 9.67 (d, 1H, amide NH); 12.04 (s, 1H, NOH).

Diastereomer 2:
Starting from 1.6 g (2.5 mmol) of diastereomer 2 from Stage 3, the p-toluenesulfonic acid salt was prepared by crystallization from 15 ml of n-propanol.

Yield: 1.4 g (66%) $[\alpha_D^{20}$=+12.7 (c=1, methanol) Melting point >200° C. (decomposition)
$^1$H-NMR (DMSO-d6, 270 MHz): δ=1.17 (s, 9H, C(CH$_3$)$_3$); 1.49 (d, 3H, OCH(CH$_3$)O); 2.29 (s, 3H, aryl CH$_3$); 3.21 (s, 3H, OCH$_3$); 3.57 (AB system, 2H, SCH$_2$); 4.13 (s, 2H, CH$_2$O); 5.22 (d, 1H, H-6); 5.82 (dd, 1H, H-7); 6.85 (s, 1H, thiazole H); 6.94 (q, 1H, OCH(CH$_3$)O); 7.08–7.16 and 7.45–7.52 (2×m, 2×2H, aromatic H); 8.4–8.9 (broad, 3H, NH$_3$); 9.68 (d, 1H, amide NH); 12.12 (s, 1H, NOH).

EMBODIMENT EXAMPLE 2:

p-Toluenesulfonate of 1-(2,2-dimethylpropionyloxy)ethyl 7-[2-(2-aminothiazol-4-yl) -2-(Z) -hydroxyiminoacetamido] -3-methoxymethyl-3-cephem-4-carboxylate (diastereomer 1)

50 g (70 mmol) of the p-toluenesulfonate of 1-(2,2-dimethylpropionyloxy)ethyl 7-[2-(2-aminothiazol-4-yl)-2-(Z)-hydroxyiminoacetamido]- 3-methoxymethyl-3-cephem-4-carboxylate (diastereomer 1/diastereomer 2=63/37) are dissolved in 65 ml of dimethylacetamide with cautious heating. The solution is added dropwise to 450 ml of n-propanol in the course of 1 hour. The mixture is stirred at room temperature for a further 4 hours to bring the crystallization to completion, and the product is filtered off with suction, washed successively with n-propanol and diisopropyl ether and dried first in air and then over phosphorus pentoxide in vacuo.

Yield: 29.5 g (59%, diastereomer 1/diastereomer 2=79/21)

After three further crystallizations from in each case 65 ml of dimethylacetamide and 450 ml of n-propanol, 8.0 g (25%) of diastereomer 1 are obtained in a purity of more than 97%.

The spectroscopic data correspond to those of diastereomer 1 in Embodiment Example 1. The diastereomer ratio is determined by means of HPLC (LiChrospher 60, RP-select B, 125×4 mm, methanol/water=5/6 with 0.12% of ammonium dihydrogen phosphate, pH=2.3; flow rate: 1 ml/minute; detection at $\lambda$=228 nm; retention times: diastereomer 1: 14.6 minutes, diastereomer 2: 11.7 minutes).

EMBODIMENT EXAMPLE 3:

Stage 1:
Sodium 3-methoxymethyl-7-phenoxyacetamido-3-cephem-4-carboxylate

The sodium salt is obtained from the carboxylic acid (Fujimoto et al., J. Antibiotics XL (1987) 370–84).

50.3 g (133 mmol) of the carboxylic acid and 11.7 g (140 mmol) of sodium bicarbonate are stirred with 900 ml of water. After filtration and freeze-drying, the sodium salt is obtained.

Yield: 47.8 g (67%)

$^1$H-NMR (D$_2$O, 270 MHz ): $\delta$=3.28 (s, 3H, OCH$_3$); 3.42 (AB system, 2H, SCH$_2$); 4.16 (AB system, 2H, CH$_2$O); 4.72 (AB system, 2H, OCH$_2$CO); 5.12 (d, 1H, H-6); 5.67 (d, 1H, H-7); 6.98–7.12 and 7.32–7.42 (2×m, 5H, aromatic H).

Stage 2:
1-(2,2-Dimethylpropionyloxy)-ethyl 3-methoxymethyl-7-phenoxyacetamido - 3-cephem-4-carboxylate 25.7 g (100 mmol) of 1-iodoethyl 2,2-dimethylpropionate are added to 42.8 g (107 mmol) of sodium 3-methoxymethyl-7-phenoxyacetamido-3-cephem-4-carboxylate in 430 ml of dry dimethylformamide. The reaction mixture is stirred at room temperature for a further hour and then poured onto a mixture of 2.5 l of water and 1.5 l of ethyl acetate. The aqueous phase is extracted again with ethyl acetate. The combined organic phases are washed with saturated sodium chloride solution, dried over magnesium sulfate and evaporated in vacuo.

Yield: 50.3 g (98%, diastereomer 1/diastereomer 2=50/50)

Stage 3:
Chromatographic diastereomer separation

The diastereomer mixture obtained in Stage 2 is separated by medium pressure chromatography (silica gel: 35–70 μm, 1 g of substance on 40 g of silica gel; toluene/ethyl acetate/diisopropyl ether=120/15/6).

Diastereomer 1:

$^1$H-NMR (DMSO-d6, 270 MHz): $\delta$=1.14 (s, 9H, C(CH$_3$)a); 1.48 (d, 3H, OCH(CH$_3$)O); 3.21 (s, 3H, OCH$_3$); 3.59 (AB system, 2H, SCH$_2$); 4.14 (s, 2H, CH$_2$O); 4.52 (d, 2H, OCH$_2$CO); 5.18 (d, 1H, H-6); 5.78 (dd, 1H, H-7); 6.87 (q, 1H, OCH(CH$_3$)O); 6.9–7.0 and 7.25–7.32 (2×m, 5H, aromatic H); 9.13 (d, 1H, amide NH).

Diastereomer 2:

$^1$H-NMR (DMSO-d6, 270 MHz): $\delta$=1.17 (s, 9H, C(CH$_3$)$_3$); 1.49 (d, 3H, OCH(CH$_3$)O); 3.22 (s, 3H, OCH$_3$); 3.60 (AB system, 2H, SCH$_2$); 4.13 (s, 2H, CH$_2$O); 4.52 (d, 2H, OCH$_2$CO); 5.18 (d, 1H, H-6); 5.75 (dd, 1H, H-7); 6.90–6.99 (m, 4H, aromatic H and OCH(CH$_3$)O); 7.20–7.32 (m, 2H, aromatic H); 9.12 (d, 1H, amide NH);.

Stage 4:
1-(2,2-Dimethylpropionyloxy )ethyl 7-amino-3-methoxymethyl-3-cephem-4-carboxylate Diastereomer 1 (p-toluenesulfonate): 1.94 g (9.32 mmol) of phosphorus pentachloride in 32 ml of anhydrous methylene chloride are added dropwise to a solution of 3.93 g (7.8 mmol) of diastereomer 1 from Stage 3 and 1.07 ml (8.45 mmol) of N,N-dimethylaniline in 39 ml of anhydrous methylene chloride at −40° C., during which the internal temperature should not rise above −25° C. The temperature is allowed to rise to −10° C. in the course of 2 hours, and 19.4 ml of iso-butanol are then added in one portion. After 10 minutes, the reaction solution is poured onto 250 ml of saturated sodium bicarbonate solution and 250 ml of ethyl acetate and the organic phase is separated off as quickly as possible. The aqueous phase is extracted again with ethyl acetate. The combined organic phases are then washed with saturated sodium chloride solution, dried over magnesium sulfate and concentrated to dryness in vacuo. The residue is dissolved in 5 ml of ethyl acetate, and a solution of 1.47 g (7.74 mmol) of p-toluenesulfonic acid monohydrate in 10 ml of ethyl acetate is added. The product is filtered off with suction, washed with ethyl acetate and dried over phosphorus pentoxide in vacuo.

Yield 2.57 g (61%)

$^1$H-NMR (DMSO-d6, 270 MHz): $\delta$=1.15 (s, 9H, C(CH$_3$)$_3$); 1.48 (d, 3H, OCH(CH$_3$)O); 2.29 (s, 3H, aryl CH$_3$); 3.23 (s, 3H, OCH$_3$); 3.69 (AB system, 2H, SCH$_2$); 4.16 (s, 2H, CH$_2$O); 5.24 and 5.28 (2×d, 2×1H, H-6 and H-7); 6.87 (q, 1H, OCH(CH$_3$)O); 7.12 (d, 2H, aromatic H); 7.49 (d, 2H, aromatic H); 8.88 (s, 2H, NH$_2$).

Diastereomer 2 hydrochloride:

Starting from 506 mg (1 mmol) of diastereomer 2 of Stage 2, the phenoxyacetyl group was split off analogously. Diastereomer 2 crystallizes as the hydrochloride from ethyl acetate.

Yield: 223 mg (55% )

$^1$H-NMR (DMSO-d$_6$), 270 MHz): $\delta$=1.17 (s, 9H, C(CH$_3$)$_3$); 1.49 (d, 3H, OCH(CH$_3$)O); 3.24 (s, 3H, OCH$_3$); 3.68 (AB system, 2H, SCH$_2$); 4.20 (s, 2H, CH$_2$O); 5.21 and 5.25 (2×d, 2×1H, H-6 and H-7); 6.93 (q, 1H, OCH(CH$_3$)O); 9.18 (s, 2H, NH$_2$).

Stage 5:
1-(2,2-Dimethylpropionyloxy)ethyl 3-methoxymethyl-7-[2-(2-tritylaminothiazol-4-yl) -2-(Z) -trityloxyiminoacetamido- 3-cephem-4-carboxylate (diastereomer 1)

1.5 g (2.75 mmol) of diastereomer 1 tosylate from Stage 4 are suspended in 100 ml of ethyl acetate and 30 ml of water. While stirring vigorously the pH is brought to 6.5 at 0° C. with saturated sodium bicarbonate solution. The organic phase is washed successively with in each case 30 ml of water and saturated sodium chloride solution, dried over sodium sulfate and concentrated to dryness in vacuo.

Yield: 1.03 g (98%)

As described in Embodiment Example 1, 1.81 g (2.3 mmol) of triethylammonium 2-(2-tritylaminothiazol-4-yl) -2-(Z)-trityloxyiminoacetate are converted into the acid chloride.

The acid chloride in 8 ml of anhydrous methylene chloride is added dropwise to a solution of 880 mg (2.3 mmol) of the ester in 10 ml of anhydrous methylene chloride at $-5°$ C. After 2 hours, the mixture is worked up as was described in Embodiment Example 1. Chromatography of the crude product using toluene/ethyl acetate (5/1) gives diastereomerically pure product.

Yield: 2.38 g (99%)

The spectroscopic data correspond to those of diastereomer 1 in Embodiment Example 1. The subsequent reactions are carried out as described in that example.

EMBODIMENT EXAMPLE 4:

1-(2,2-Dimethylpropionyloxy)ethyl 7-amino-3-methoxymethyl-3-cephem-4-carboxylate, diastereomer 1 tosylate and diastereomer 2 hydrochloride As described for Stage 4 in Embodiment Example 3, starting from 3.03 g (6 mmol) of 1-(2,2-dimethylpropionyloxy)ethyl-3-methoxymethyl-7-phenoxyacetamido-3-cephem-4-carboxylate (diastereomer 1/diastereomer 2=52/48), the phenoxyacetyl group is split off. The dried organic phases are concentrated to 10 ml. On cooling to 0° C., diastereomer 2 precipitates out as the hydrochloride and is filtered off with suction (yield: 759 mg=31%). 1.13 g (5.9 mmol) of p-toluenesulfonic acid monohydrate in 5 ml of ethyl acetate are added to the mother liquor. The toluenesulfonic acid salt which has precipitated out is filtered off with suction, washed with a little ethyl acetate and dried over phosphorus pentoxide in vacuo. Yield: 667 mg (23%)

According to HPLC, the content of diastereomer 1 is more than 97 percent (HPLC: LiChrospher 100 RP-18, 5 µm, 125×4 mm, flow rate: 1 ml/minute, detection at $\lambda$=254 nm, water/methanol=52/48 with 0.1% of ammonium acetate, retention times: diastereomer 1: 12.1 minutes, diastereomer 2: 11.8 minutes).

The conversion of the intermediate stage into the end product has already been described in the preceding embodiment examples.

EMBODIMENT EXAMPLE 5

1-(2,2-Dimethylpropionyloxy)ethyl 7-amino-3-methoxymethyl- 3-cephem-4-carboxylate, diastereomer 1 p-toluenesulfonate 3.12 ml (21 mmol) of DBU are added to a suspension of 4.88 g (20 mmol) of 7-amino-3-methoxymethyl-3-cephem-4-carboxylic acid in 200 ml of anhydrous methylene chloride at 0° C. 4.99 g (24 mmol) of 1-bromoethyl 2,2-dimethylpropionate are added to the slightly cloudy, yellow solution and the mixture is then stirred at room temperature for 3 hours. The reaction solution is poured onto 600 ml of saturated sodium bicarbonate solution and 800 ml of methylene chloride. The organic phase is washed with saturated sodium chloride solution, dried over sodium sulfate and evaporated in vacuo. The crude product (9.3 g) is dissolved in 15 ml of ethyl acetate, and 1.9 g (10 mmol) of p-toluenesulfonic acid monohydrate in 10 ml of ethyl acetate are added. The product which has precipitated out is filtered off with suction, washed with diisopropyl ether and dried in vacuo.

Yield: 3.95 g (36%) of diastereomer 1/diastereomer 2=85/15

Recrystallization of the salt from n-propanol gives pure diastereomer 1, which is further reacted as described.

EMBODIMENT EXAMPLE 6:

1-(2,2-Dimethylpropionyloxy)ethyl 7-amino-3-methoxymethyl-3-cephem-4-carboxylate, diastereomer 1 tosylate and diastereomer 2 hydrochloride As described in Embodiment Example 5, the crude product is prepared from 4.88 g (20 mmol) of 7-amino-3-methoxymethyl-3-cephem-4-carboxylic acid. The oil thus obtained is dissolved in 20 ml of ethyl acetate, and a freshly prepared solution of 0.65 ml (9.2 mmol) of acetyl chloride and 1.07 ml (18.4 mmol) of ethanol in 5 ml of ethyl acetate is added. The hydrochloride which has precipitated out in an ice-bath is filtered off with suction, washed with ethyl acetate and dried.

Yield: 2.57 g (32%), diastereomer 1/diastereomer 2=22/78

A solution of 1.75 g (9.2 mmol) of p-toluenesulfonic acid monohydrate in 8 ml of ethyl acetate is added to the filtrate and the precipitate which has separated out is filtered off with suction.

Yield: 1.15 g (16%), diastereomer 1/diastereomer 2=97/3

The spectroscopic data correspond to those in Embodiment Example 3.

EMBODIMENT EXAMPLE 7

Stage 1:

1-(2,2-dimethylpropionyloxy)ethyl 3-methoxymethyl-7-[(naphth-2-yl)-methylideneamino]-3-cephem-4-carboxylate (diastereomer mixture)

As described in Embodiment Example 5, the crude ester is prepared from 2.44 g (10 mmol) of 7-amino-3-methoxymethyl-3-cephem-4-carboxylic acid. The oil thus obtained is dissolved in 30 ml of anhydrous methylene chloride, and a solution of 1.56 g (10 mmol) of naphthalene-2-carbaldehyde in 40 ml of toluene is added. After 3 hours at room temperature, the mixture is diluted with 40 ml of toluene and washed three times with 30 ml of water each time. The solution is dried over magnesium sulfate and concentrated to dryness in vacuo. Stage 2:

Chromatographic separation of the diastereomers

The crude product from Stage 1 is chromatographed on 500 g of silica gel (pH 7.5). For this, commercially available silica gel (35–70 µm) is suspended in water, and dilute sodium hydroxide solution is added until the pH remains constant at 7.5. The silica gel is filtered off with suction, washed with methanol and dried at 110° C./20 torr for 18 hours. First 1.7 g (33%) of diastereomer 1 and then 1.65 g (32%) of diastereomer 2 are eluted with toluene/ethyl acetate (20/1). Diastereomer 1 crystallizes from methanol as colorless needles of melting point 110° C.

Diastereomer 1:

$^1$H-NMR (CDCl$_3$, 270 MHz): $\delta$=1.22 (s, 9H, C(CH$_3$)s; 1.58 (d, 3H, CH-CH$_3$); 3.22 (s, 3H, OCH$_3$); 3.57 (s, 2H, SCH$_2$); 4.31 (AB system, 2H, CH$_2$O); 5.21 (d, 1H, H-6); 5.50 (dd, 1H, H-7); 6.99 (q, 1H, CH-CH$_3$); 7.52 (mc, 2H, aromatic H), 7.88 (mc, 3H, aromatic H); 8.03 (mc, 3H, aromatic H); 8.78 (d, 1H, CH=N).

Diastereomer 2:

1H-NMR (CDCl$_3$, 270 MHz): $\delta$=1.22 (s, 9H, C(CH$_3$)$_3$); 1.58 (d, 3H, CH-CH$_3$); 3.32 (s, 3H, OCH$_3$); 3.52 (s, 2H, SCH$_2$); 4.26 (AB system, 2H, CH$_2$O); 5.26 (d, 1H, H-6); 5.49 (dd, 1H, H-7); 7.02 (q, 1H, CH-CH$_3$); 7.51 (mc, 2H, aromatic H), 7.84 (mc, 3H, aromatic H); 8.02 (mc, 3H, aromatic H); 8.75 (d, 1H, CH=N).

The Schiff's bases are split into the pure diastereomers of 7-amino-3-methoxymethyl-3-cephem-4-carboxylate 1-(2,2-dimethylpropionyloxy)ethyl with Girard T reagent by a procedure analogous to literature specifications (for example Kamachi et al., The Journal of Antibiotics XLI (11) (1988), 1602–1616).

We claim:

1. A crystalline acid addition salt consisting essentially of a pure crystalline acid addition salt of 1-(2,2-dimethylpropionyloxy)ethyl 3-cephem-4-carboxylate of the formula II

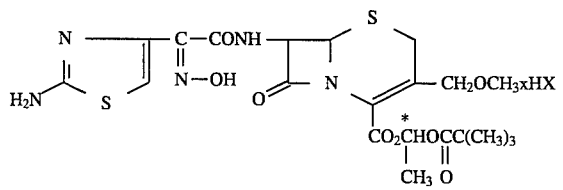

wherein the C atom labelled with * has the 1(S)-configuration, wherein the group =N—OH is in the syn-position, and wherein X is the anion of a physiologically acceptable, monobasic or polybasic, inorganic or organic acid.

2. The crystalline acid addition salt of claim 1, wherein HX is benzenesulfonic acid, p-toluenesulfonic acid or 4-ethylbenzenesulfonic acid.

3. A pharmaceutical formulation which is active against bacterial infections, comprising a pharmaceutically effective amount of the crystalline acid addition salt of claim 1 and at least one pharmaceutically acceptable excipient or diluent.

4. A method for combating a bacterial infection comprising administering to a host in recognized need thereof the crystalline acid addition salt of claim 1 in a dosage effective for combating bacterial infections.

* * * * *